(12) United States Patent
Proksch

(10) Patent No.: US 7,434,445 B2
(45) Date of Patent: Oct. 14, 2008

(54) APPARATUS FOR DETERMINING CANTILEVER PARAMETERS

(75) Inventor: Roger Proksch, Santa Barbara, CA (US)

(73) Assignee: Asylum Research Corporation, Santa Barbara, CA (US)

( * ) Notice: Subject to any disclaimer, the term of this patent is extended or adjusted under 35 U.S.C. 154(b) by 310 days.

(21) Appl. No.: 11/426,567

(22) Filed: Jun. 26, 2006

(65) Prior Publication Data

US 2007/0062252 A1    Mar. 22, 2007

Related U.S. Application Data

(63) Continuation-in-part of application No. 10/087,196, filed on Feb. 28, 2002, now Pat. No. 7,066,005.

(60) Provisional application No. 60/272,697, filed on Feb. 28, 2001.

(51) Int. Cl.
*G01B 21/00* (2006.01)

(52) U.S. Cl. .......................... 73/1.79; 73/1.89

(58) Field of Classification Search ................ 73/1.79, 73/1.89, 105, 579; 250/252.1; 356/614; 702/42, 56, 116, 150

See application file for complete search history.

(56) References Cited

U.S. PATENT DOCUMENTS

| | | | |
|---|---|---|---|
| 4,771,237 A | 9/1988 | Daley | 73/1.79 X |
| 5,412,980 A | 5/1995 | Elings et al. | 73/105 |
| 5,898,106 A * | 4/1999 | Babcock et al. | 73/105 |
| 5,978,743 A | 11/1999 | Kiyono | 702/80 |
| 6,142,006 A | 11/2000 | Marchon et al. | 73/1.89 X |
| 6,279,389 B1 * | 8/2001 | Adderton et al. | 73/105 |
| 6,323,483 B1 * | 11/2001 | Cleveland et al. | 250/306 |
| 6,357,285 B1 * | 3/2002 | Allen | 73/105 |
| 6,567,752 B2 | 5/2003 | Cusumano et al. | 702/116 X |
| 6,853,187 B2 * | 2/2005 | Fainchtein | 324/300 |
| 6,958,816 B1 | 10/2005 | Dogariu et al. | 356/479 |
| 2002/0152795 A1 | 10/2002 | Guerraa-Vela et al. | 73/1.89 |
| 2005/0011256 A1 * | 1/2005 | Hoh | 73/105 |

(Continued)

OTHER PUBLICATIONS

Butt, H-J, et al., "Scan Speed Limit in Atomic Force Microscopy," J. Microscopy, vol. 169, No. 1, pp. 75-84, 1993.

(Continued)

*Primary Examiner*—Thomas P Noland
(74) *Attorney, Agent, or Firm*—Morgan, Lewis & Bockius LLP

(57) ABSTRACT

Apparatus for determining physical properties of micromachined cantilevers used in cantilever-based instruments, including atomic force microscopes, molecular force probe instruments and chemical or biological sensing probes. The properties that may be so determined include optical lever sensitivity, cantilever spring constant and cantilever sample separation. Cantilevers characterized with the method may be used to determine fluid flow rates. The apparatus measures cantilever deflection resulting from drag force as the cantilever is moved through fluid. Unlike other methods for determining such physical properties of cantilevers, the method described does not depend on cantilever contact with a well-defined rigid surface. Consequently, the apparatus may be employed in situations where such contact is undesirable or inconvenient. The apparatus may be used for applications such as molecular force measurements, atomic force microscopy and manipulation technology, chemical or biological sensing, nanometer scale surface profiling, and other aspects of nanotechnology.

8 Claims, 10 Drawing Sheets

U.S. PATENT DOCUMENTS

2006/0058607 A1* 3/2006 Garcia-Webb et al. ...... 600/407

OTHER PUBLICATIONS

Butt, H-J, et al., "Calculation of Thermal Noise in Atomic Force Microscopy," Nanotechnology, vol. 6, pp. 1-7, 1995.

Cleveland, J.P., et al., "Nondestructive Method for Determining the Spring Constant of Cantilevers for Scanning Force Microscopy," Rev. of Sci. Instrum., vol. 64, No. 2, pp. 403-405, 1993.

Drummond, C.J., et al., "Characterisation of the Mechanical Properties of Thin Film Cantilevers with the Atomic Force Microscopy," Materials Science Forum, vols. 189-190, pp. 107-114, 1995.

Gibson, C.T., et al., "Determination of the Spring Constants of Probes for Force Microscopy/Spectroscopy," Nanotechnology, vol. 7, No. 3, pp. 259-262, 1996.

Hutter, J.L., et al., "Erratum: Calibration of Atomic-Force Microscope Tips," Rev. Sci. Instrum., vol. 64, No. 11, pp. 3342, Nov. 1993.

Miyatani, T., et al., "Calibration of Surface Stress Measurements with Atomic Force Microscopy," Appl. Phys., vol. 81, No. 11, pp. 7099-7115, Jun. 1997.

Neumeister, J.M., et al., "Lateral, Normal, and Longitudinal Spring Constants of Atomic Force Microscopy Cantilevers," Rev. Sci. Instrum., vol. 65, No. 8, pp. 2527-2531, 1994.

Ogletree, D.F., et al., "Calibration of Frictional Forces in Atomic Force Microscopy," Rev. Sci. Instrum., vol. 67, No. 9, pp. 3298-3306, Sep. 1996.

Sader, J.E., et al., "Method for Calibration of Atomic Force Microscope Cantilevers," Rev. Sci. Instrum., vol. 66, No. 7, pp. 3789-3798, Jul. 1995.

Sader, J.E., "Frequency Response of Cantilever Beams Immersed in Viscous Fluids with Applications to the Atomic Force Microscope," J. of Appl. Phys., vol. 84, No. 1, pp. 64-76, Jul. 1998.

Sader, J.E., et al., "Calibration of Rectangular Atomic Force Microscope Cantilevers," Rev. Sci. Instrum., vol. 70, No. 10, pp. 3967-3969, 1999.

Scholl, D., et al., "In Situ Force Calibration of High Force Constant Atomic Force Microscope Cantilevers," Rev. Sci. Instrum., vol. 65, No. 7, pp. 2255-2257, Jul. 1984.

Senden, T.J., et al., "Experimental Determination of Spring Constants in Atomic Force Microscopy," Langmuir, vol. 10, No. 4, pp. 1003-1004, 1994.

Torii, A., et al., "A Method for Determining the Spring Constant of Cantilevers for Atomic Force Microscopy," Meas. Sci. Technol., vol. 7, No. 2, pp. 179-184, 1996.

Walters, D.A., et al., "Short Cantilevers for Atomic Force Microscopy," Rev. Sci. Instrum., vol. 67, Issue 10, pp. 3583-3590, 1996.

* cited by examiner

US 7,434,445 B2

APPARATUS FOR DETERMINING CANTILEVER PARAMETERS

CROSS-REFERENCE TO RELATED APPLICATIONS

This application is a continuation-in-part of U.S. patent application Ser. No. 10/087,196, filed Feb. 28, 2002, issued as U.S. Pat. No. 7,066,005 on Jun. 27, 2006, which claims priority to U.S. Provisional Application No. 60/272,697, filed on Feb. 28, 2001, the disclosures of which are incorporated fully herein by reference.

BACKGROUND OF THE INVENTION

The present invention relates generally to methods for determining physical properties of micro-machined cantilevers used in cantilever-based instruments, including atomic force microscopes (AFM's), molecular force probe instruments and chemical or biological sensing probes. It also involves using cantilevers characterized with such methods to measure fluid flow rates.

Calibrating the sensitivity of cantilevers used in cantilever-based instruments is critical for correctly interpreting the results obtained from such instruments. The foundation of this calibration is the determination of the optical sensitivity of the cantilever, the relationship between deflection of the cantilever and movement of the tip of the cantilever in the z direction. For this purpose, deflection of the cantilever is measured with the optical detection means common in such instruments, a position sensor collecting light reflected off the back of the cantilever. Knowing the optical sensitivity of the cantilever, the spring constant of the cantilever may be readily calculated.

The conventional methods for determining optical lever sensitivity have either been destructive or required that the lever be brought into hard contact with a well defined rigid surface. Because the distances are typically less than one micron, and the relative positions of the cantilever tip and such a surface difficult to locate, making such contact is far from a trivial proposition. The difficulty of the procedure is enhanced by the fact that slippage of the tip laterally over the surface introduces serious errors.

Even if the conventional methods were easy of execution, there are many instances when it is not desirable or convenient to measure optical lever sensitivity by touching a surface. When the results depend on chemical or biological sensitization of the cantilever tip, or if the tip is particularly sharp, hard contact or any contact before performing the experiment may compromise the results. Similarly compromising may be hard contact when the sample is coated on the surface and is a soft material such as cells. Finally, in the case of chemical or biological sensing probes, there may not be a rigid surface anywhere near the cantilever against which to press.

Two methods for determining optical lever sensitivity not requiring hard contact with a well-defined rigid surface have been proposed, but each has important limitations and is as yet untested. D'Costa and Hoh proposed estimation of optical lever sensitivity by moving the spot across the position sensor a known distance. Because it is not sensitive to actual motion of the cantilever, this method does not account for differences in cantilever geometry or changes in the alignment of the spot on the lever. These issues become even more critical as the length scale of cantilevers shrink. Sader proposes to rely on a plan view of the lever and the measured resonant frequency and quality factor to estimate optical lever sensitivity spring constant.

Although there has been a large amount of work dedicated to the cantilever calibration issue, the precision of the resulting techniques seems to be limited to 10%. In this situation, it is desirable to make use of another method to check for consistency.

SUMMARY OF THE INVENTION

An object of the present invention is to provide a simple method for calibrating the sensitivity of any type of cantilever used in cantilever-based instruments without making contact with any surface.

A second object is to provide a method for the cantilever to approach a sample surface in a gentle and repeatable manner.

Another objective is to provide a method for calibrating the sensitivity of cantilevers that is easily automated.

Another objective is to measure fluid flow rates using micromachined cantilevers.

These and other objects are achieved according to the present invention by (i) measuring the deflection of the cantilever as it moves at a measured velocity through a fluid, (ii) determining the resonant frequency and quality factor of the cantilever by measuring its power spectrum and (iii) deriving optical lever sensitivity from combining these measurements.

DESCRIPTION OF EMBODIMENTS

Figure 9:
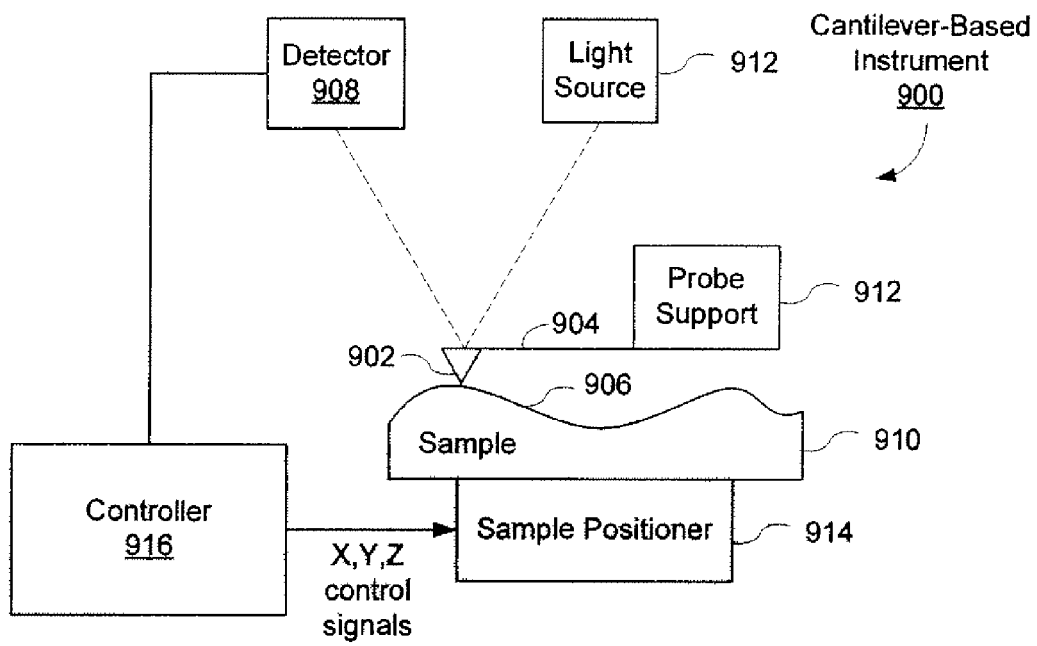
FIG. 9 is a block diagram of a contact mode cantilever-based instrument, such as an atomic force microscope (AFM) or scanning tunneling microscope (STM).

FIG. 9 shows a cantilever-based instrument 900, such as an atomic force microscope (AFM), which operates by placing a sharp tip 902 attached to a bendable cantilever 904 directly on a surface 906 and then scanning the surface laterally using a sample positioner 914 directed by a controller 916. The bending of the cantilever 904 in response to surface height variations of the surface 906 is monitored by a detector 908. Typically, the height of the fixed end of the cantilever relative to the surface 906 of the sample 910 is adjusted with feedback to maintain the bending of the cantilever 904 at a predetermined amount during lateral scanning. The adjustment amount versus lateral position creates a map of the surface 906. The deflection detection system typically uses an optical beam, produced by a light source 912, and a detector 908. Using very small microfabricated cantilevers and piezoelectric positioners as lateral and vertical scanners, AFM's can have resolution down to molecular level, and may operate with controllable forces small enough to image biological substances.

Contact cantilever-based instruments, such as the one shown in FIG. 9, has found many applications. However, for samples that are very soft or interact strongly with the tip, such as photoresist, some polymers silicon oxides, many biological samples, and others, the contact mode has drawbacks.

Figure 10:
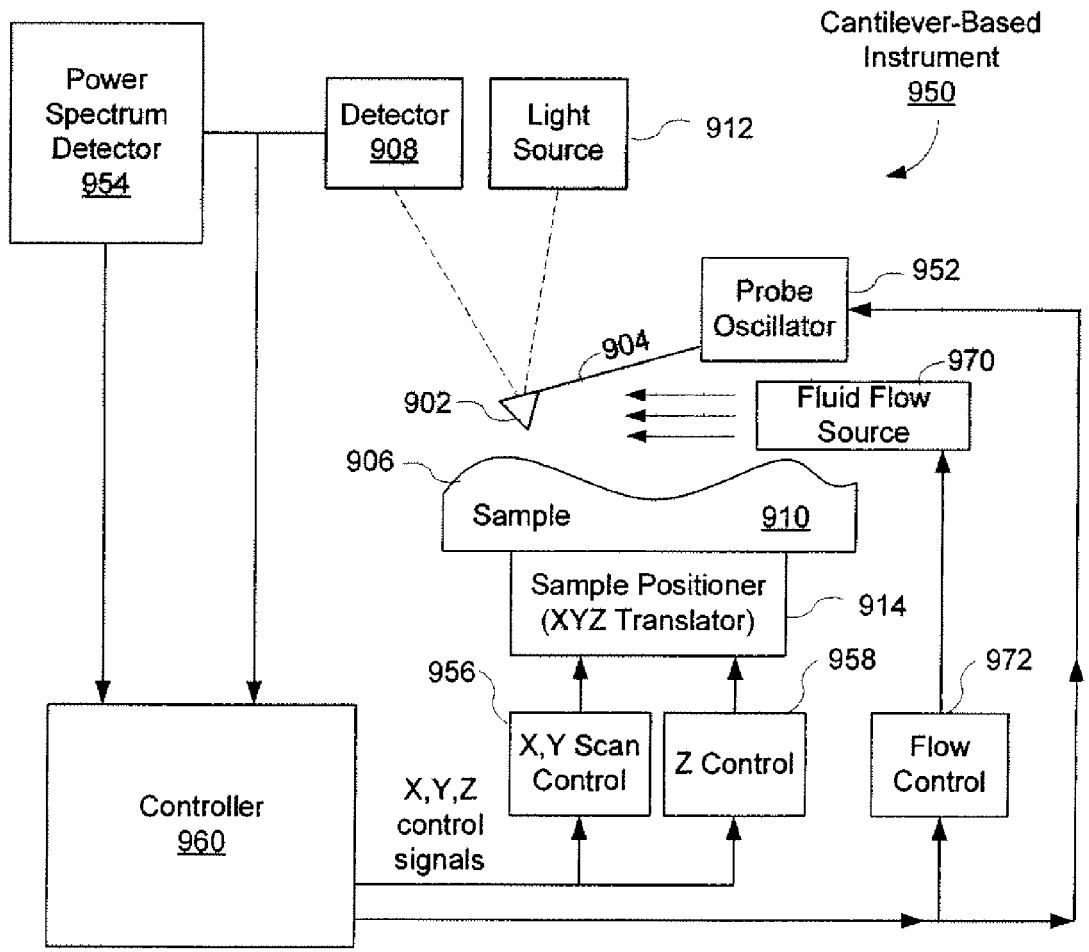
FIG. 10 is a block diagram of a cantilever-based instrument, including a probe positioning apparatus, a tip oscillator and a fluid flow control apparatus.

FIG. 10 shows a non-contact cantilever-based instrument 950, such as a non-contact atomic force microscope (AFM), profiles the surface 906 of a sample 910 in a different fashion than the contact cantilever-based instrument. In the non-contact cantilever-based instrument 950, the tip 902 is scanned above the surface, and the very weak Van der Waals attractive forces between the tip and sample are sensed. The cantilever 904 may be vibrated by a probe oscillator 952 at a small amplitude and brought near to the surface 906 of the sample 910 such that the force gradient due to interaction between the tip 902 and surface 906 modifies the spring constant of the cantilever 904 and shifts its natural resonant frequency. The shift in resonance will change the cantilever's response to the vibration source in a detectable fashion. The frequency shift may be measured by a power spectrum detector 954. The shift in resonance frequency may be used to map the surface, for example by adjusting the probe surface separation during lateral scanning to maintain a predetermined shift from resonance. Lateral scanning is accomplished using a sample positioner 914 whose lateral (XY) movement may be controlled by an XY scan control circuit 956, which in turn is controlled by a controller 960 for the instrument 950. The height of the sample 910 may be controlled by a Z control circuit 958, which receives commands from the instrument controller 960 and directs control signals to the sample positioner 914.

The cantilever-based instrument 950 may also include a fluid flow source 970, for providing air or other fluid to flow past the cantilever tip 902, in accordance with commands received by a flow control circuit 972 from the instrument controller 960.

Figure 11:
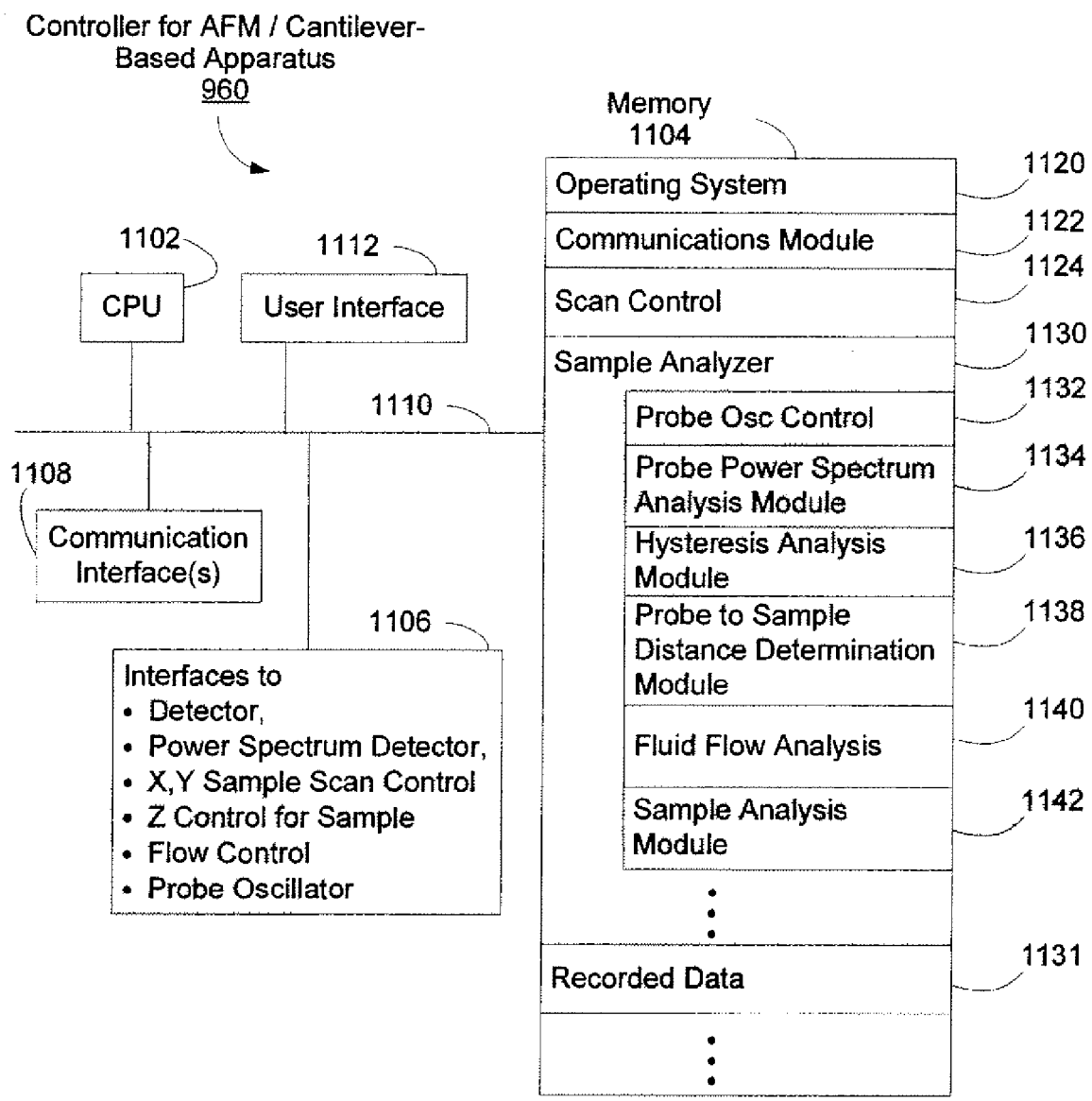
FIG. 11 is a block diagram of a controller for the cantilever-based instrument of FIG. 10.

An exemplary controller 960 for the cantilever-based instrument 950 (FIG. 10) is shown in schematic form in FIG. 11. The controller 960 may include one or more central processing units (CPU's) 1102 for executing stored programs, memory 1104 for storing executable programs and other information, interfaces 1106 for sending commands and receiving information to and from the control circuits and sensors of the instrument (e.g., the detector 908, the probe oscillator 952, the power spectrum detector 954, the XY scan control circuit 956, the Z control circuit 958, the flow control circuit 972), an optional communication interface 1108 for communicating with other computers via a communications network (e.g., a local area network, the Internet, or combination of communication networks), a user interface 1112, and one or more communication busses 1110 for interconnecting the aforementioned components. The communication buses 1110 may include circuitry (sometimes called a chipset) that interconnects and controls communications between system components. The user interface 1112 may include a display, a keyboard, and possibly other components (e.g., control buttons, knobs, and/or sliders, etc.) as well.

Memory 1104 includes high-speed random access memory, such as DRAM, SRAM, DDR RAM, or other random access solid state memory devices; and may include non-volatile memory, such as one or more magnetic disk storage devices, optical disk storage devices, or other non-volatile solid state storage devices. In some embodiments, memory 1104 stores the following programs, modules, and data structures, or a subset thereof:

- an operating system 1120 that includes procedures for handling various basic system services and for performing hardware dependent tasks;
- a communications module 1122 that is used for connecting the instrument 950 (FIG. 10) to other computers or devices via the one or more communication interfaces 1108 and one or more communication networks, such as the Internet, other wide area networks, local area networks, metropolitan area networks, and so on;
- a scan control application (or set of instructions) 1124 for controlling the scanning of the surface of a sample, and optionally for controlling other components of the instrument as well;
- a sample analysis module, suite of procedures or set of instructions 1130; and
- recorded data 1131, obtained during the scanning of the surface of a sample.

The sample analysis module 1130 may include one or more of the following programs, modules or sets of instructions:

- a probe oscillator control program (or set of instructions) 1132,
- a probe power spectrum analysis module (or set of instructions) 1134 for determining the power spectrum and/or resonance frequency of a cantilever,
- a hysteresis analysis module (or set of instructions) 1136 (e.g., for determining a hysteresis of the deflection of the cantilever 904 of the instrument as a function of position of the based on the cantilever),
- a probe to sample distance determination module (or set of instructions) 1138,
- a fluid flow analysis procedure or module (or set of instructions) 1140 (e.g., for determining a fluid flow rate), and
- optionally, one or more additional sample analysis modules 1142 or instrument control programs.

Each of the modules or procedures identified above with reference to FIG. 11 may be stored in one or more of the previously mentioned memory devices. The applications, functions, modules and operating systems shown in FIG. 11 correspond to sets of instructions for performing the functions described above. The above identified modules or programs (i.e., sets of instructions) need not be implemented as separate software programs, procedures or modules, and thus various subsets of these modules may be combined or otherwise rearranged in various embodiments. In some embodiments, memory 1104 may store a subset of the modules and data structures identified above. Furthermore memory 1104 may store additional modules and data structures not described above.

The optical sensitivity of the micromachined cantilever, the derivative of the change in cantilever deflection with respect to change in the z position of the cantilever tip (typically abbreviated as "OLS"), is the foundation for correctly interpreting the results obtained from cantilever-based instruments. FIG. 1A depicts one of the conventional methods for determining OLS. As shown in FIG. 1A, the cantilever is pressed into a hard surface (typically freshly cleaved mica) by the instrument (not shown) and moved an arbitrary distance measured by the instrument. Deflection of the cantilever resulting from this change in position is measured with optical detection means commonly employed in such instruments: low coherence light is focused onto the back of the cantilever with an adjustable focus lens and the light reflecting off the cantilever is collected by an adjustable mirror and guided onto position sensor. The position sensor provides a voltage that is proportional to the deflection of the cantilever.

Figure 1B:
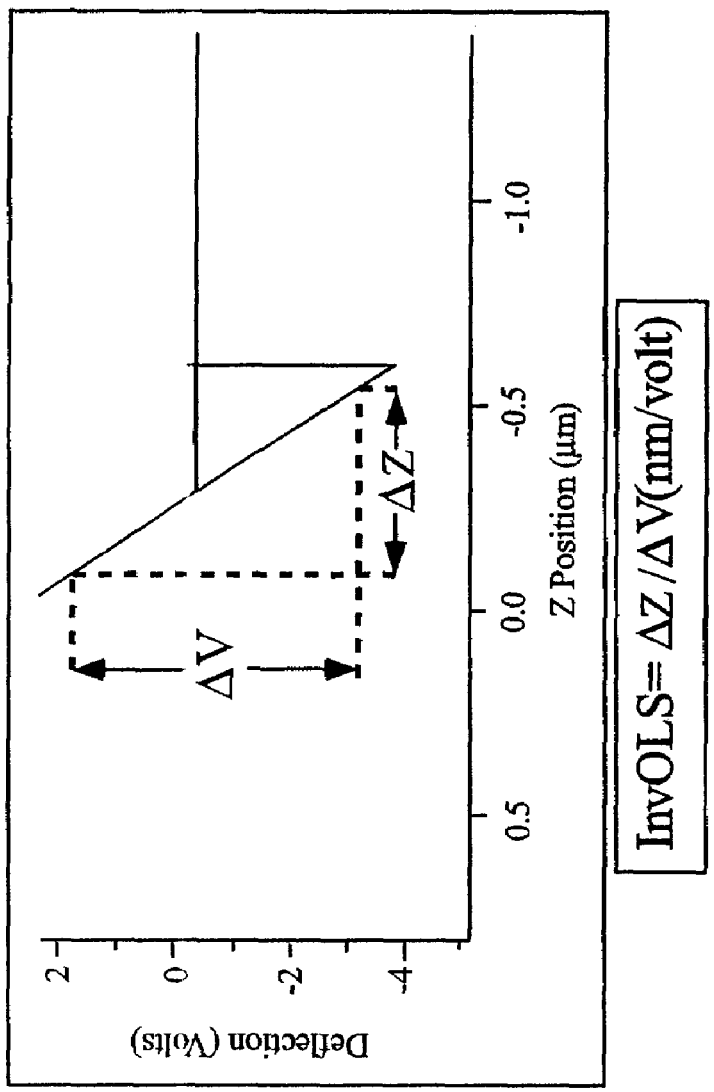
FIG. 1B shows a graphical representative of cantilever deflection in relation to a distance (Z) between the cantilever and the surface of FIG. 1A.
Figure 1A:
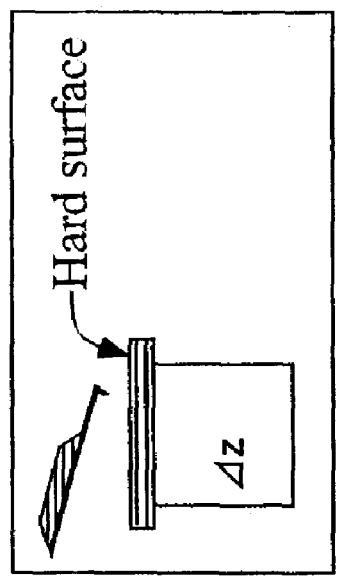
FIG. 1A depicts a simplified plane view of cantilever to be placed in contact with a hard surface for calculating optical lever sensitivity according to previous methods.

FIG. 1B graphs the deflection of the cantilever vs. the z position of the tip. As shown in FIG. 1B, it is typical to calculate optical sensitivity as the inverse of OLS ("InvOLS"), the derivative of change in the z position of the cantilever tip with respect to change in cantilever deflection.

Knowing InvOLS permits us to calculate the cantilever spring constant, k, from the Equipartition of Energy Theorem:

$$\frac{1}{2}k_B T = \frac{1}{2}k \langle A^2 \rangle \qquad (1)$$

where $k_B$ is Boltzmann's constant, T is the temperature, k is the cantilever spring constant and $\langle A^2 \rangle$ is the mean squared cantilever amplitude ($\langle A^2 \rangle = \text{InvOLS}^2 \cdot \Delta V^2$, where $\Delta V$ is cantilever deflection in volts).

As previously noted, it is not always desirable or convenient to determine InvOLS by making hard contact with a well-defined rigid surface as shown in FIG. 1A. The invention disclosed here permits determination of InvOLS without touching a surface by measuring cantilever deflection resulting from drag force as the cantilever is moved through a fluid (including air).

Figure 2:
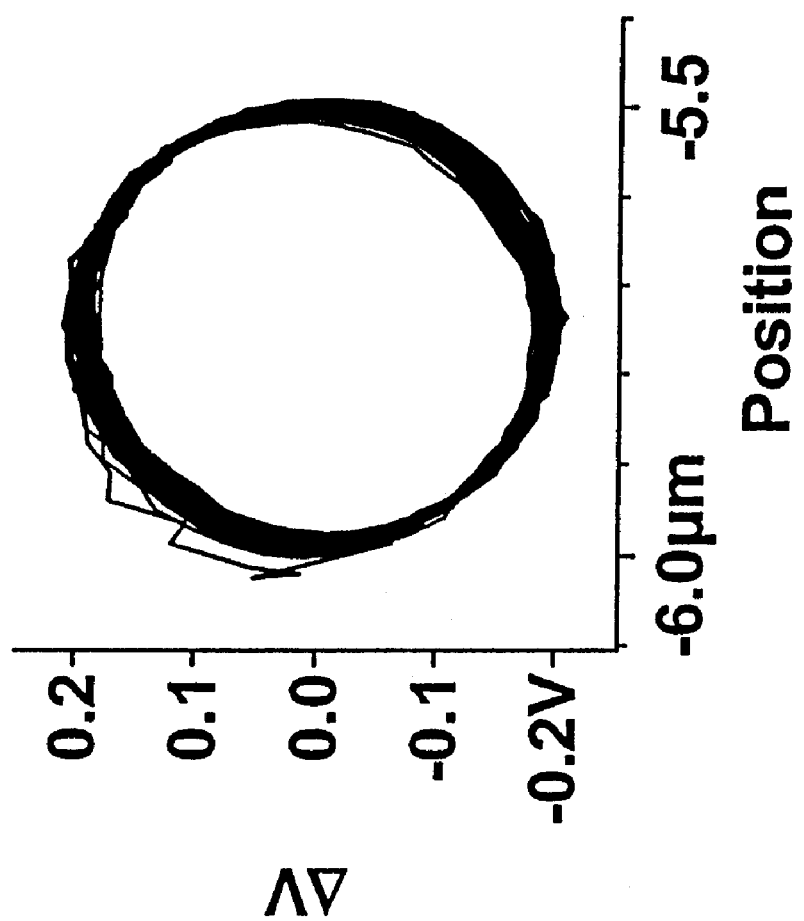
FIG. 2 depicts a graphical representation of a measured hysteresis of deflection resulting from oscillating a cantilever.

A cantilever moving through a fluid will be deflected by a viscous drag force. The measured cantilever deflection is converted to a force using $F_{hyst} = k \cdot \text{InvOLS} \cdot \Delta V$, where $\Delta V$ is cantilever deflection in volts as measured by the position sensor. If the cantilever is moving at a speed v through the fluid, we can characterize the dissipative force, which absent turbulence is equal to the drag force, as $F_{hyst} = -b_{hyst} v$, with $b_{hyst}$ being the damping coefficient. FIG. 2 shows a typical hysteresis loop measured by a 40 Hz sinusoidal cycling of the base position of a cantilever while monitoring cantilever deflection with a position sensor.

An independent measurement of the damping coefficient can be made by observing the thermal fluctuations of the cantilever. The simple harmonic oscillator model gives the damping coefficient in terms of the spring constant k, the resonant frequency $\omega_0$ and the quality factor Q as:

$$b_{therm} = \frac{k}{\omega_0 Q} \qquad (2)$$

Figure 3:
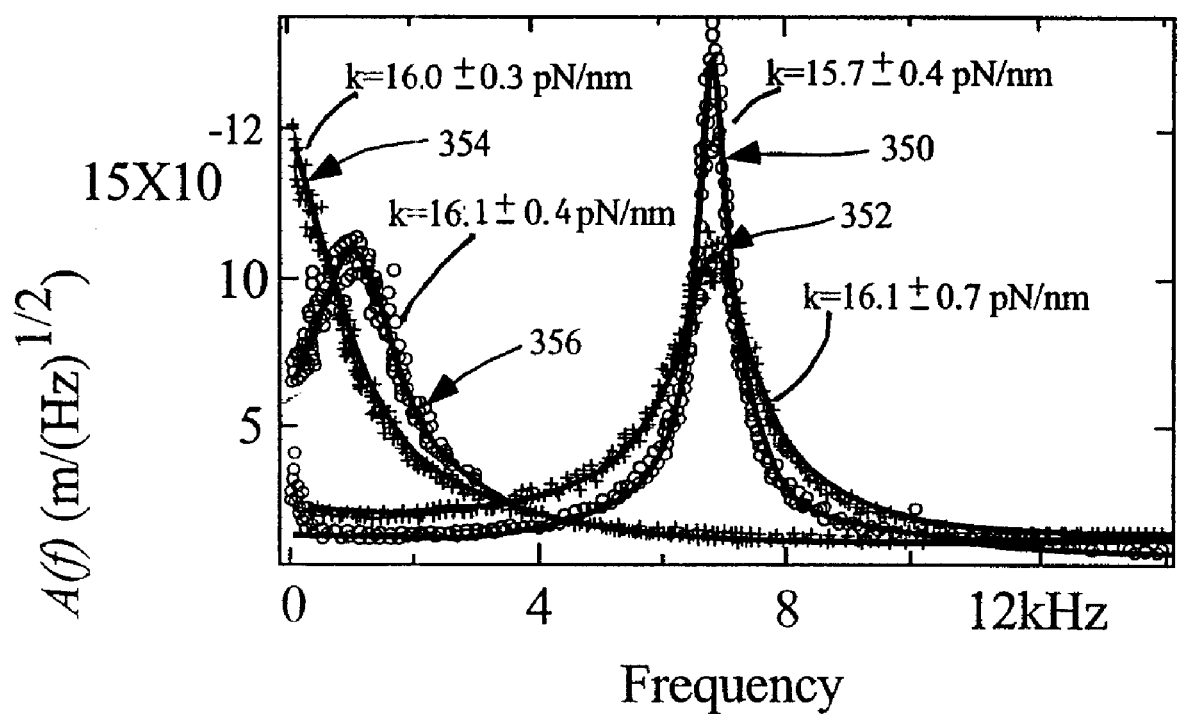
FIG. 3 depicts a graphical representation of a power spectrum for a plurality of cantilever exposed to various environmental conditions during oscillation of the cantilever.

FIG. 3 shows four power spectra of cantilevers in fluid. The two high frequency curves 350, 352 were made in air, where a first measurement depicted by the first curve 350 was performed with the cantilever relatively far away from the surface, and the second measurement depicted by the second curve or spectrum 352 was performed with the cantilever relatively close to the surface. The second spectrum 352 taken close to the surface had increased damping, yielding a peak with a lower quality factor. The third and fourth curves 354, 356 with low peak frequencies were taken in fluid, which caused the resonance to be significantly damped. The fluid is also carried along with the lever as it moves, creating an effective mass that lowers the resonant frequency. The measured spring constants of the four levers (using the method of Hutter and Bechoefer, which requires hard contact with a surface) are virtually the same despite the different environments.

From the data derived from the calculation of such power spectra, and using Equation 2, the damping coefficient, $b_{therm}$, may be calculated. In some embodiments, the power spectra is calculated through a computer means, such as a computer or processor.

As is well known (see for example, Landau and Lifschitz, *Fluid Mechanics*), damping is a complicated function of the geometry of the damped system, fluid properties and the amplitude and frequency of the motion. However, for micromachined cantilevers in cantilever-based instruments, we have found experimentally that the thermal and hysteretic damping coefficients are related by $b_{hyst} = \kappa \cdot b_{therm}$, where $\kappa$ is a phenomenological factor that depends on the fluid properties drive frequency, tip-sample separation and the specific lever geometry. This relationship between the thermal and hysteretic damping coefficients allows us to combine the expressions for viscous drag force and dissipative force in an expression for InvOLS, all in terms of variables measured away from a surface:

$$\text{InvOLS}_{hyst} = \frac{\kappa v}{\omega_0 Q \Delta V} \qquad (3)$$

Once $\text{InvOLS}_{hyst}$ has been determined, the spring constant can be calculated from the rearranged Equipartition of Energy Theorem:

$$k = \frac{k_B T}{\text{InvOLS}^2 \Delta V^2} \qquad (4)$$

Figure 4:
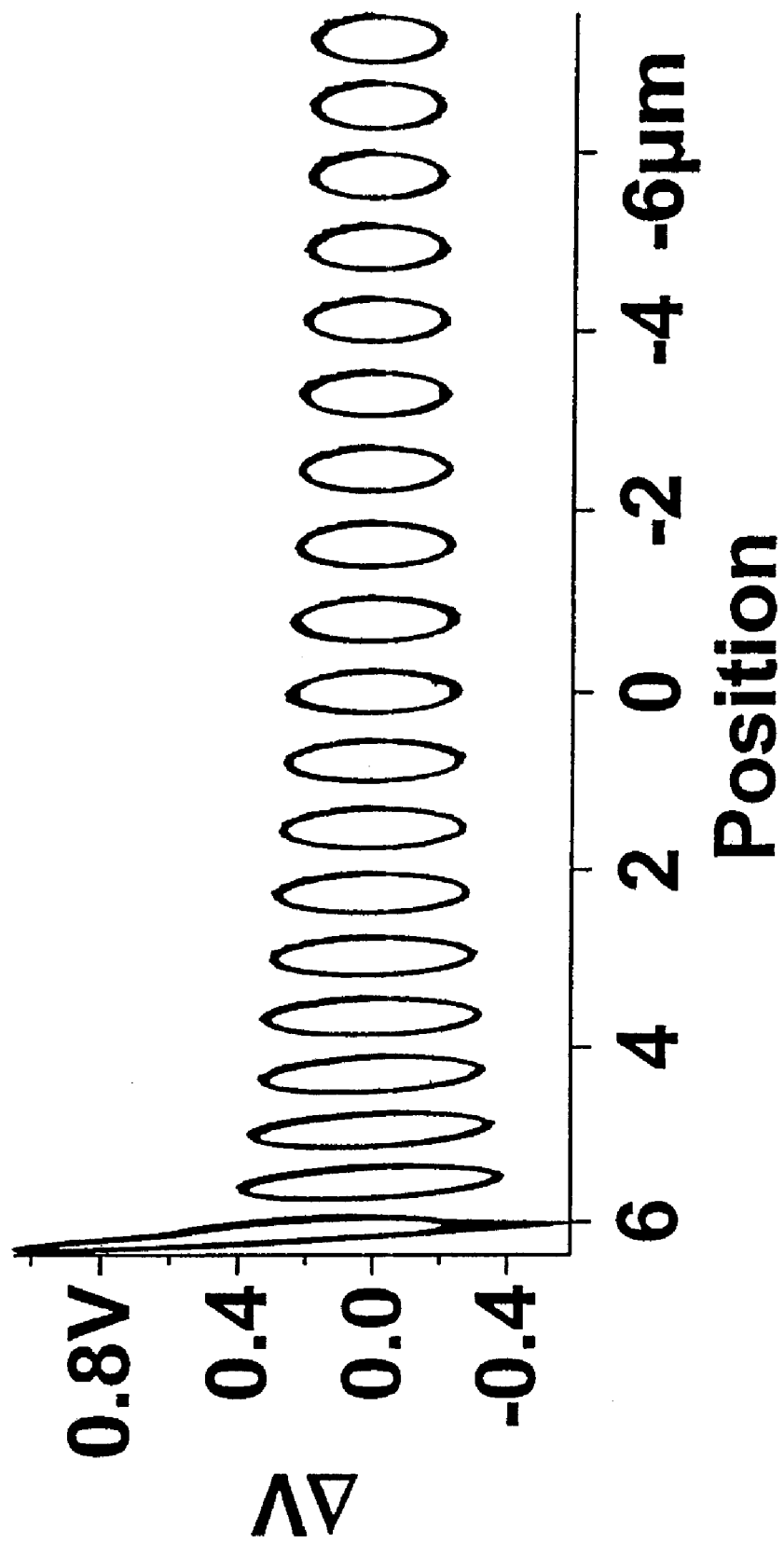
FIG. 4 depicts a graphical representation of a plurality of measured hysteresis loops as a cantilever base is moved relative to a surface.
Figure 5A:
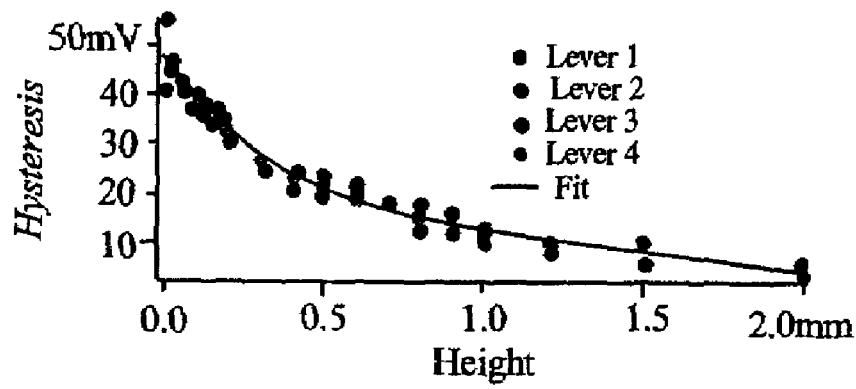
FIG. 5A depicts a graphical representation of a amplitude of hysteretic damping as a function of cantilever tip separation from a surface for a plurality of cantilevers over a range of cantilever base excitation amplitudes and frequencies.
Figure 5B:
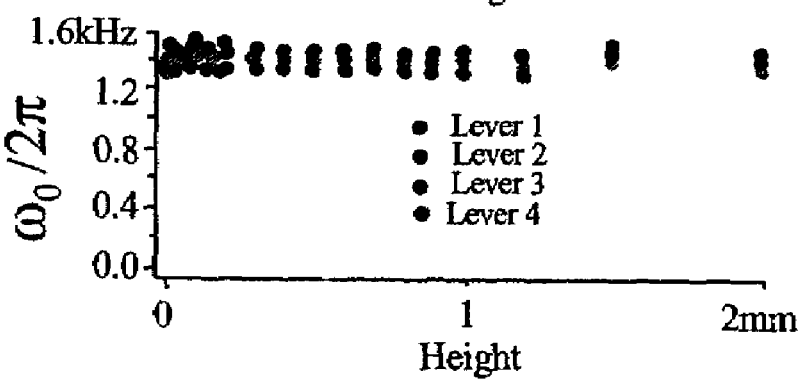
FIG. 5B depicts a graphical representation of a resonant frequency measured with thermal noise as a function of the tip sample separation for a series of cantilevers.
Figure 5C:
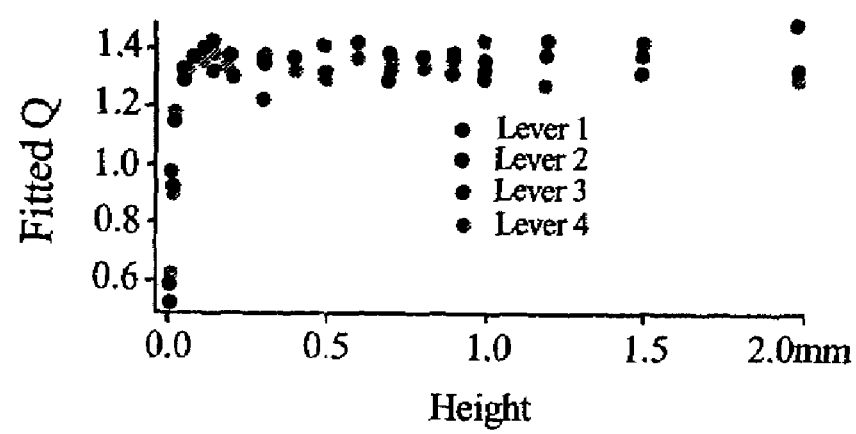
FIG. 5C depicts a graphical representative of a quality factor as a function of tip sample separation for a plurality of cantilevers.
Figure 6:
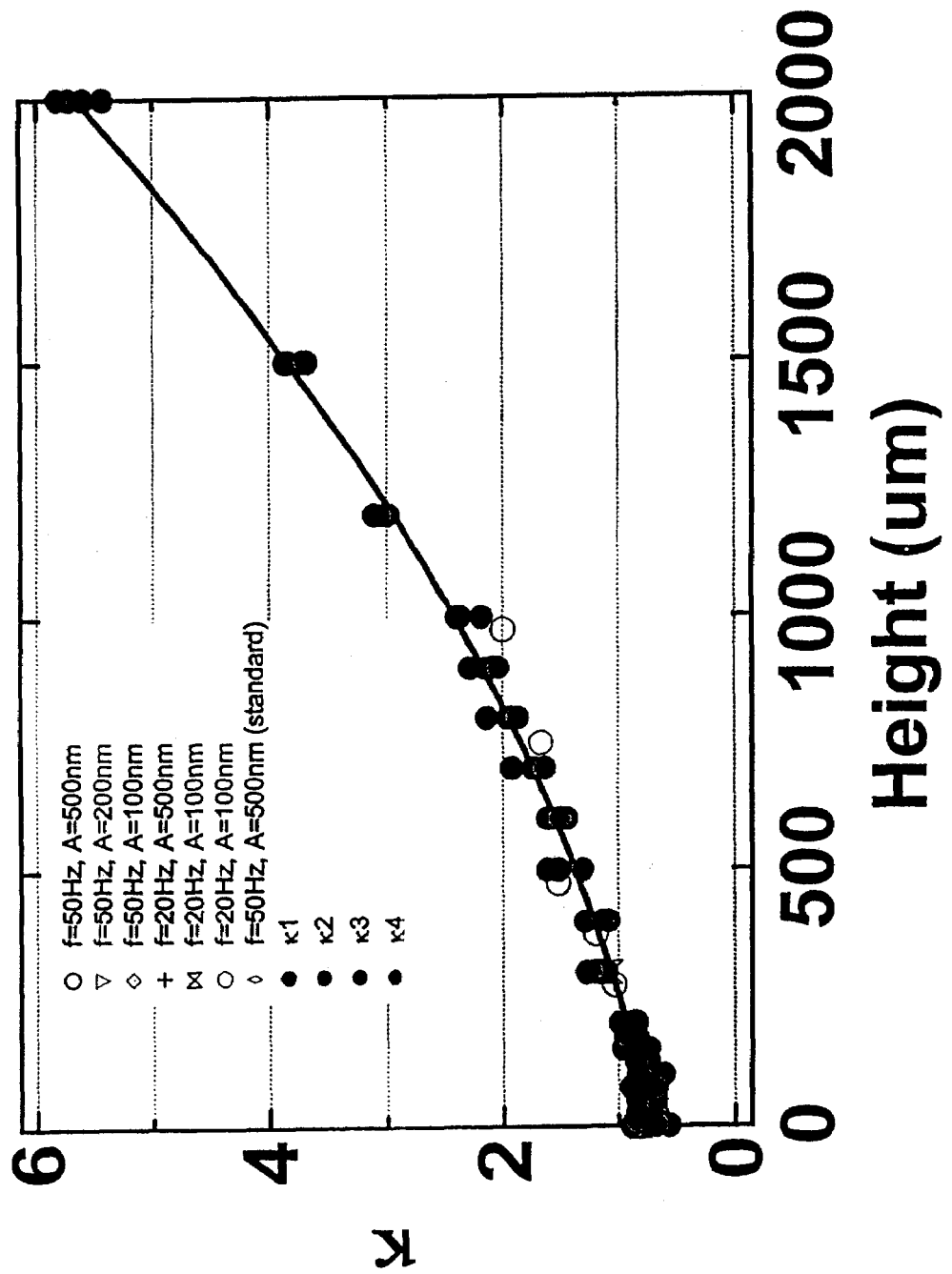
FIG. 6 depicts a graphical representation of a phenomenological factor as a function of cantilever tip separation from a surface for a plurality of different amplitudes, frequencies and cantilevers.

FIG. 4 shows a series of hysteresis loops measured at different cantilever tip-sample separations ($\Delta Z$). It is shown that measurements taken as the tip of the cantilever approaches the surface (towards the left of the Figure), the damping increases, until, in the last loop, intermittent contact with the surface is made. FIG. 5A shows the amplitude of the hysteretic damping as a function of tip-sample separation for a range of cantilever base excitation amplitudes and frequencies. These data were extracted from a number of measurements similar to those shown in FIG. 4. FIG. 5B shows the resonant frequency measured with thermal noise as a function of the tip sample separation for a series of similar triangle cantilevers. FIG. 5C shows the quality factor Q measured in a similar fashion as a function of tip-sample separation. The x-axis in all three graphs extends out to 2 mm. It is apparent that the three quantities, cantilever deflection in volts $\Delta V$ (FIG. 5A), quality factor Q (FIG. 5B) and resonant frequency $\omega_0$ (FIG. 5C) have differing dependences on tip-sample separation. This implies that $\kappa$ is a function of tip-sample separation. FIG. 6 shows $\kappa$ as a function of tip-sample separation for eleven different amplitudes, frequencies and cantilevers. These measurements imply that $\kappa$ has a predictable behavior, at least for a particular lever in the amplitude and frequency range tested in this work. The curve in FIG. 6 can then be used in conjunction with Equation 3 to predict InvOLS and, via Equation 4, the spring constant of the lever.

Figure 7:
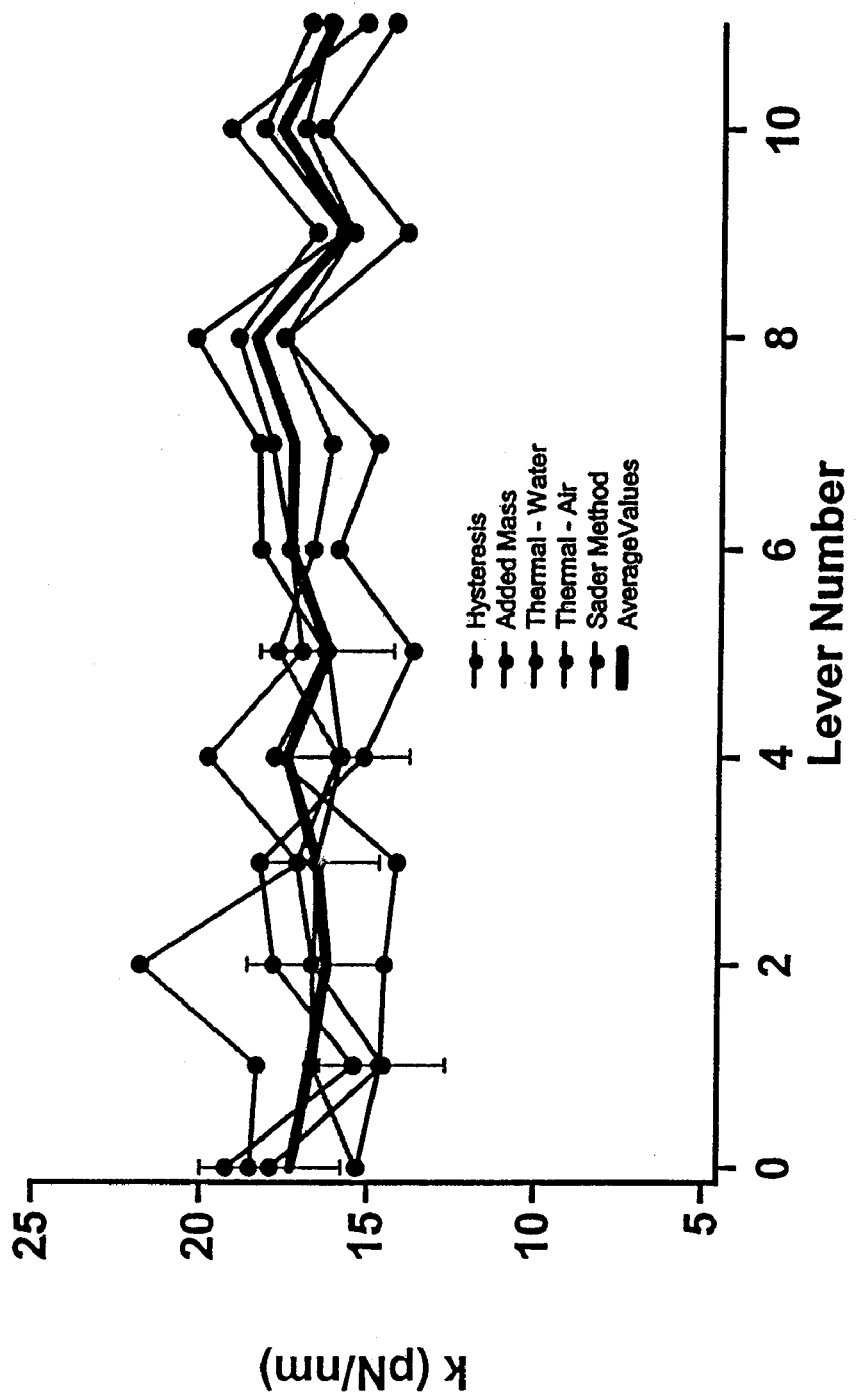
FIG. 7 depicts a graphical representation of spring constants for a plurality of cantilevers utilizing a plurality of different methods for calculating the spring constants, including the method according to the present invention.
Figure 7:

FIG. 7 shows five separate calculations of cantilever spring constants for 12 different cantilevers using five different methods, including the hysteretic method disclosed here, as well as the average of all calculations. The variation is pronounced, but each method yields a result generally within 20% of any other.

Figure 8:
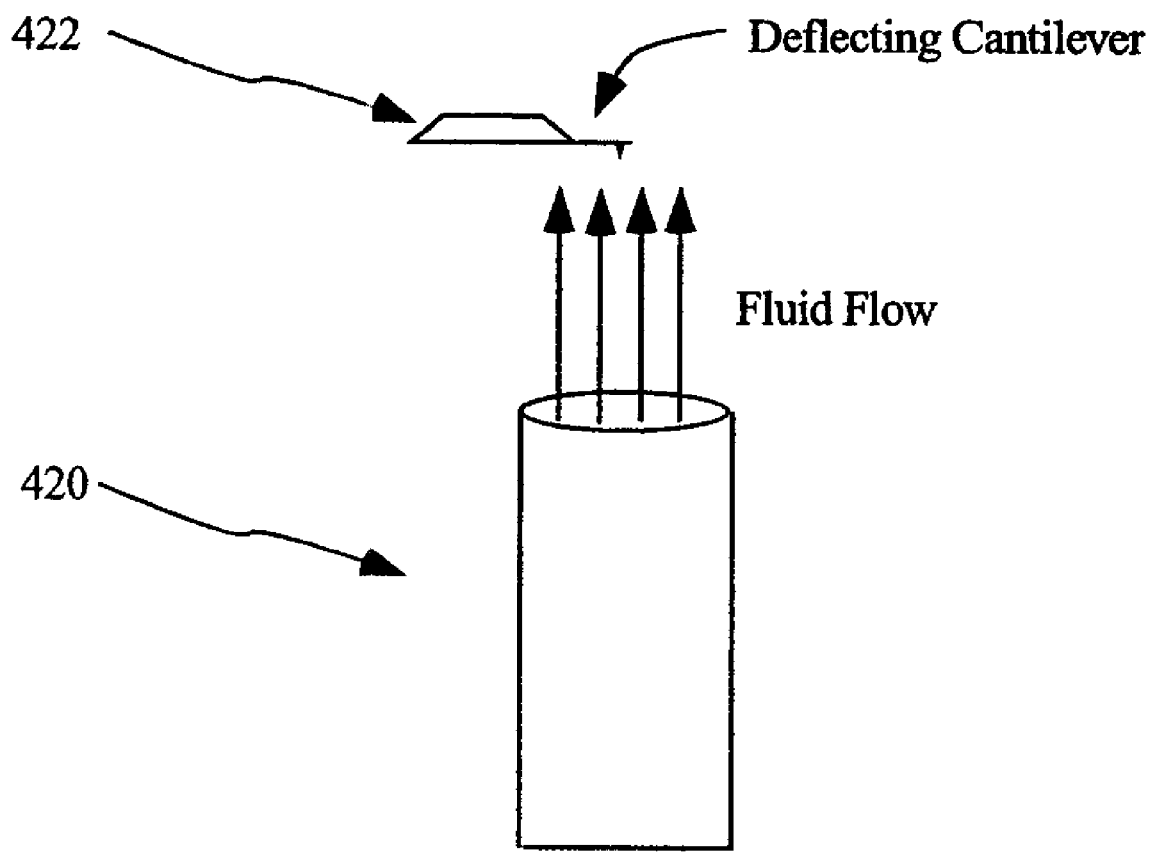
FIG. 8 depicts a simplified block diagram of an apparatus for measuring a fluid flow rate.

In one embodiment of the present invention, the fluid flow around the cantilever is induced by moving the base of the cantilever. It is also possible, and in some situations desirable, to induce fluid flow around the lever with some other method, such as an external pump or perfusion apparatus. FIG. 8 schematically illustrates such an arrangement, where the fluid flow 420 is controlled by (n external apparatus to flow over the cantilever 422.

The measurement of hysteresis loops while monitoring cantilever deflection required for determining InvOLS in the disclosed method, has an additional benefit. Because the cantilever damping changes as a function of tip-sample separation (see FIG. 4 and the plotted amplitude of hysteresis in FIG. 5A) observing these hysteresis curves allows the position of the surface to be determined without actually making contact with the sample. The increasing hysteresis as the cantilever approaching the surface allows the surface to be approached to within a few microns without actually making contact. This has utility, for example, in atomic force microscopy where gently bringing the cantilever tip into proximity with the surface is a common challenge.

It is to be noted that if instead of the above situation, the spring constant and damping constant were known but the fluid flow speed was not, the drag measurement would yield a value for the fluid flow rate past the lever via the relationship $$v = \frac{b_{hyst}}{k \cdot \Delta V \cdot InvOLS}.$$

This can be used as a probe of fluid flow as illustrated in FIG. 8.

The described embodiments of the invention are only considered to be preferred and illustrative of the inventive concept. The scope of the invention is not to be restricted to such embodiments. Various and numerous other arrangements may be devised by one skilled in the art without departing from the spirit and scope of the invention.

What is claimed is:

1. An apparatus for determining cantilever parameters, comprising:
    means for measuring a drag force acting on a cantilever by monitoring a deflection of the cantilever;
    means for determining a power spectrum of the cantilever;
    means for measuring motion of a base of the cantilever; and
    means for determining one or more characteristics of the cantilever based on the motion of the base, the power spectrum, and the cantilever deflection.

2. The apparatus of claim 1, including means for directing a fluid flow over the cantilever;
    wherein the means for determining characteristics includes means for determining a fluid flow rate of the fluid flow.

3. The apparatus of claim 2, wherein the means for determining the fluid flow rate is configured to determine the fluid flow rate based at least in part on a spring constant and dampening constant of the cantilever.

4. The apparatus of claim 3, including means for oscillating the cantilever;
    wherein:
    the means for monitoring the deflection is configured to monitor the deflection of the cantilever while oscillating;
    the means for determining characteristics is configured to determine a hysteresis of the deflection of the cantilever as a function of position of the base of the cantilever.

5. The apparatus of claim 1, including means for oscillating the cantilever;
    wherein:
    the means for monitoring the deflection is configured to monitor the deflection of the cantilever while oscillating; and
    the means for determining characteristics includes a means for determining a spring constant based at least in part on the power spectrum associated with the cantilever.

6. The apparatus of claim 5, wherein the means for monitoring the deflection includes means for determining a hysteresis of deflection of the cantilever and for monitoring the hysteresis; and
    the means for determining characteristics is further configured to determine a distance between the cantilever tip and the surface based at least in part on the hysteresis.

7. The apparatus of claim 1, wherein the means for monitoring the deflection is configured to determine a hysteresis of deflection of the cantilever and to monitor the hysteresis; and
    the means for determining characteristics is configured to determine a distance between the cantilever tip and the surface.

8. The apparatus of claim 1, wherein the means for monitoring the deflection is configured to determine a hysteresis of deflection of the cantilever and to monitor the hysteresis; and
    the means for determining characteristics is configured to determine dissipation between the cantilever tip and the surface in accordance with the hysteresis of deflection of the cantilever.

* * * * *